United States Patent [19]

Smith

[11] 4,148,874

[45] Apr. 10, 1979

[54] DERMATOLOGICAL COMPOSITIONS

[75] Inventor: Donald E. Smith, Hamilton, Ohio

[73] Assignee: The Procter & Gamble Company, Cincinnati, Ohio

[21] Appl. No.: 910,269

[22] Filed: May 30, 1978

Related U.S. Application Data

[60] Division of Ser. No. 805,668, Jun. 13, 1977, which is a division of Ser. No. 647,943, Jan. 12, 1976, Pat. No. 4,046,886, which is a division of Ser. No. 541,902, Jan. 17, 1975, Pat. No. 3,952,099, which is a division of Ser. No. 340,787, Mar. 13, 1973, Pat. No. 3,896,238, which is a continuation-in-part of Ser. No. 241,404, Apr. 5, 1972, abandoned.

[51] Int. Cl.$^2$ .............. A61K 7/34; A61K 7/36; A61K 7/38; A61K 31/10

[52] U.S. Cl. .................. 424/66; 424/67; 424/68; 424/337; 424/358; 424/361

[58] Field of Search ............ 424/66–68, 424/337, 358, 361

[56] References Cited

U.S. PATENT DOCUMENTS

| | | | |
|---|---|---|---|
| 3,232,879 | 1/1966 | Len | 252/131 |
| 3,247,258 | 4/1966 | Anderson | 260/607 |
| 3,288,858 | 11/1966 | Lyness et al. | 260/607 |
| 3,326,768 | 6/1967 | Kilmer-Macmillan | 424/65 |
| 3,527,864 | 9/1970 | Kilmer-Macmillan | 424/177 |
| 3,551,554 | 12/1970 | Herschler | 424/7 |
| 3,678,156 | 6/1972 | Kilmer-Macmillan et al. | 424/68 |
| 3,739,031 | 6/1973 | Priestley et al. | 260/607 |
| 3,896,238 | 7/1975 | Smith | 424/358 |
| 3,952,099 | 4/1976 | Smith | 424/227 |
| 4,046,886 | 9/1977 | Smith | 424/227 |

FOREIGN PATENT DOCUMENTS 943174 12/1963 United Kingdom.

OTHER PUBLICATIONS

Schwartz et al., J. Am. Oil. Chem. Soc. 42(9), 800–804 (1965).
CA.56:4882ce (1962), 60:1536(b) (1964), 74:79479x (1971), CA. 74:102950(a) (1971).
CA. 75:25345(c) (1971), CA. 54:13561g (1960), CA. 54:14579c (1960), CA. 69:99370p (1968), CA. 70:50450 (1969).

Primary Examiner—Shep K. Rose
Attorney, Agent, or Firm—Jerry J. Yetter; Julius P. Filcik; Richard C. Witte

[57] ABSTRACT

Compositions for enhancing the penetration of pharmacologically active agents through skin comprising a sugar ester in combination with a sulfoxide or phosphine oxide.

1 Claim, No Drawings

DERMATOLOGICAL COMPOSITIONS

CROSS REFERENCE TO RELATED APPLICATION

This is a division of application Ser. No. 805,668 filed June 13, 1977 which is a divisional of application Ser. No. 647,943, filed Jan. 12, 1976, now U.S. Pat. No. 4,046,886, which is a divisional of application Ser. No. 541,902, filed Jan. 17, 1975, now U.S. Pat. No. 3,952,099 (Apr. 20, 1976), which is a divisional of application Ser. No. 340,787, filed Mar. 13, 1973, now U.S. Pat. No. 3,896,238 (July 22, 1975), which is a continuation-in-part of Ser. No. 241,404, filed Apr. 5, 1972, now abandoned.

BACKGROUND OF THE INVENTION

This invention relates to compositions for topical application to animals (this term as used herein includes both humans and lower animals) tissue, said compositions providing enhanced penetration of various pharmacologically active substances into or through such tissue.

The epidermal barrier to percutaneous absorption, i.e., the stratum corneum, is a nearly impermeable heterogeneous animal tissue of which keratin is a major component. This tissue is found in animal skin and mucosal tissue such as tongue, gingiva, esophagus, and vagina. A wide variety of pharmacologically active substances are desirably applied topically to this epithelial tissue for an essentially local effect achieved upon penetration into or through the stratum corneum. For example, compositions used in the treatment of a variety of dermatoses, including acne vulgaris, tinea versicolor, acne rosacea and other skin maladies associated with hyperplasia of the infected sebaceous gland, are desirably treated by topical medications. Likewise, eczema and eczema-like skin disorders caused by excessive cell proliferation are treated by topical application of ointments and salves. Localized inflammation which often accompanies arthritis and bursitis is treated by topical medications, as is common muscular "strain" caused by overexertion. Topical anesthetics are widely used in medicine and dentistry. The cosmetic efficacy of a variety of agents such as antiperspirants, rubifacients and emollients depends on the ability of the cosmetic agents to penetrate the epidermal barrier. Accordingly, it is seen that any means whereby the penetration of pharmacologically active agents through skin can be enhanced is of substantial interest.

It is known that various surface-active compounds improve the activity of pharmacologically active substances, apparently by enhancing the penetration of same through skin. For example, U.S. Pat. No. 3,326,768 discloses that the presence of a phosphine oxide surfactant in antiperspirant compositions containing anticholinergic compounds appears to increase activity by providing more efficient absorption of the active agents at the site of application. U.S. Pat. No. 3,527,864 discloses the use of alkyl sulfoxides to enhance the penetration of a variety of pharmacologically active agents through skin. The co-pending application of Warren I. Lyness and James Scala entitled "Compositions for Topical Application to Animal Tissue and Method of Enhancing Penetration Thereby", Ser. No. 230,040, filed Feb. 28, 1972, relates to the use of phosphine oxides to enhance the penetration of a variety of agents through skin.

Many surface-active compounds enhance the permeability of skin by actually damaging the barrier tissue. Indeed, the degree of penetration enhancement appears in some cases to be proportional to the extent of tissue damage. Certain organic solvents serve to enhance penetration of substances through the epidermal barrier. For example, dimethyl sulfoxide (DMSO) and homologous low molecular weight sulfoxides, when used in solvent concentrations, e.g., 50% or more, will enhance penetration of various substances; see U.S. Pat. No. 3,551,554. However, such compounds are systemically distributed in a very short time and can cause undesirable symptoms at these higher concentrations.

While the foregoing higher sulfoxides and phosphine oxides are suitable for enhancing skin penetration, improved compositions providing a greater degree of penetration and improved clinical efficacy are desirable. It is, therefore, an object of this invention to provide improved compositions for topical application to animal tissue and an improved method for enhancing the penetration of pharmacologically active substances through such tissue. It is a further object to provide a method of enhancing the penetration of pharmacologically active substances into or through animal tissue, especially skin, without damaging said tissue or causing adverse systemic effects. These and other objects are obtained herein as will be seen from the following disclosure.

SUMMARY OF THE INVENTION

The present invention encompasses compositions adapted to topical application to animal tissue, said compositions providing enhanced penetration of all manner of pharmacologically active agents through said tissue. The tissue penetration enhancing compositions of this invention comprise: (1) at least about 0.1% by weight of a sugar ester of the type hereinafter disclosed; and (2) at least about 0.1% by weight of a compound selected from the group consisting of alkyl sulfoxides of the formula $R^1S(O)R^2$ wherein $R^1$ is a straight chain or branched chain alkyl, alkenyl, substituted alkyl, heteroalkyl or hydroxy-substituted alkyl substituent containing from 4 to 12 carbon atoms and $R^2$ is a low molecular weight ($C_1$–$C_8$) alkyl or low molecular weight ($C_1$–$C_8$) hydroxy-substituted alkyl substituent; and phosphine oxides of the formula $R^3R^4R^5P(O)$ wherein $R^3$ is an alkyl, aralkyl, substituted alkyl, heteroalkyl, hydroxy-substituted alkyl substituent containing from 1 to 12 carbon atoms or aryl (e.g., phenyl, tolyl) containing 6 to 9 carbon atoms, and $R^4$ and $R^5$ are each low molecular weight alkyl ($C_1$–$C_4$) or low molecular weight hydroxy-substituted alkyl ($C_1$–$C_4$) substituents. Preferably, the compositions herein also contain a pharmaceutically acceptable carrier. As will be seen hereinafter, the pharmaceutically acceptable carrier can be deleted from the formulations in certain instances, e.g., when the low molecular weight liquid phosphine oxides are employed.

The above composition comprising the sugar ester and sulfoxide or phosphine oxide compound is applied to animal tissue in conjunction with a safe and effective amount of a pharmacologically active agent to enhance the penetration of said agent through animal tissue, especially skin, thereby providing a method aspect of the instant invention.

Of course, admixture of the skin penetration enhancing composition hereinabove noted with the pharmacologically active agent provides a pharmacologically active composition especially adapted to topical application to skin. In general, such compositions comprise: (1) at least about 0.1% by weight of a sugar ester; (2) a safe and effective amount (usually at least about 0.1% by weight) of a pharmacologically active agent; and (3) at least about 0.1% by weight of a sulfoxide or phosphine oxide compound of the type disclosed above. Preferably, these compositions also contain a pharmaceutically acceptable carrier.

By the term "pharmacologically active agent" as used herein is meant any chemical material or compound suitable for topical administration which induces any desired local transitory effect on living structures (i.e., animal tissue) contacted therewith (sometimes referred to as "penetrant"). Such substances include, for example, antimicrobials, including antibiotics, as well as antihistamines, local anesthetics, steroids, sunscreens, vitamins, elemental sulfur, various astringent metal ions such as aluminum, iron, zirconium and zinc, which metal ions provide antiperspirants, anti-inflammatories, anti-metabolites, rubifacients and the like.

By the term "pharmaceutically acceptable carrier" as used herein is meant any liquid, gel, solvent, liquid diluent, fluid ointment base, fluid suppository base and the like, which is suitable for use in contact with living animal tissue without any untoward physiological response and which does not interact with the other components of the composition in a deleterious manner and which can be used to establish the compositions herein in their preferred liquid form.

The "enhanced penetration" effected through the use of the compositions of this invention can be observed, for example, by measuring the rate of diffusion of the pharmacologically active substances through guinea pig skin using the diffusion cell apparatus, described in U.S. Pat. No. 3,527,864.

DETAILED DESCRIPTION OF THE INVENTION

The compositions of this invention contain as an essential ingredient at least about 0.1%, preferably about 0.1% to about 1.0% by weight, of a sugar ester of the type hereinafter disclosed. While concentrations substantially greater than 1%, i.e., 50% and greater, of the said sugar esters can be present in such compositions, this represents an economic waste inasmuch as the increased concentrations do not result in an concomitant increase in the penetration enhancing properties of the compositions.

The sugar esters suitable for use in this invention can be classified as hydrocarbyl and alkyl polyoxyalkylene esters of cyclic polyhydroxy saccharides wherein one or more of the hydroxyl groups on the saccharide moiety is substituted with an acyl or polyoxyalkylene group. Hydrocarbyl sugar esters can be prepared in well-known fashion by heating an acid or acid halide with a sugar, i.e., by a simple esterification reaction. When an acid halide is used to prepare the sugar esters it is preferable to have an organic base, e.g., pyridine, morpholine, and the like, present in the reaction system. The reaction proceeds to form the sugar ester and the base hydrohalide. Acid chlorides, bromides and iodides are suitable for preparing the sugar esters used herein; the acid chlorides are preferred. In an alternate procedure, a lower alkyl ester of the carboxylic acid is heated with the sugar to form the sugar ester and a lower alcohol. When this process is used, the ethyl, methyl and propyl esters of the carboxylic acid can be employed.

The sugars employed in the preparation of the sugar esters used in the instant compositions include monosaccharides, di-saccharides and oligo-saccharides well-known in the art. As examples of the various kinds of sugars useful in the preparation of the sugar esters herein there may be mentioned the dextrorotatory and levorotatory forms of glucose, fructose, mannose, galactose, arabinose and xylose. Typical di-saccharides include maltose, cellibiose, lactose, and trehalose. Typical tri-saccharides include raffinose and gentianose. The di-saccharides are preferred for use in the preparation of the sugar esters used in the compositions of this invention. Sucrose is especially preferred for this purpose.

Sucrose is typical of the di-saccharides used to prepare the sugar esters employed herein and has the formula:

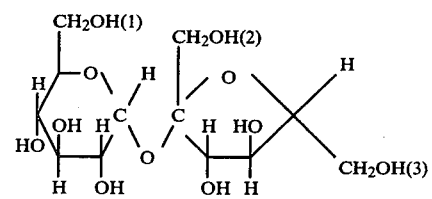

Sucrose can be esterified at one or more of its eight hydroxyl groups in the hereinabove described manner to provide the sucrose esters useful herein. When sucrose is combined with an esterification agent in a 1:1 mole ratio, sucrose mono-esters are formed; when the ratio of esterification agent to sucrose is 2:1, or greater, the di-, tri-, etc., esters are formed, up to a maximum of the octa-ester. A similar situation obtains in the preparation of sugar esters using the other sugars noted above.

Preferred sugar esters herein are those prepared by the esterification of sugars at a mole ratio of esterification agent:sugar of 1:1 and 2:1, i.e., the mono-acyl and di-acyl sugar esters. Especially preferred are the mono-acyl and di-acyl sugar esters wherein the acyl substituents contain from about 8 to about 20 carbon atoms. Of the mono-acyl and di-acyl sugar esters, the respective esters of di-saccharide sugars, especially sucrose, wherein the acyl groups contain from about 8 to about 20 carbon atoms are especially preferred. Sucrose monooleate has been found to be particularly efficacious in the compositions herein.

Sucrose monooleate, the preferred sugar ester in the compositions of this invention, can be prepared by admixing sucrose and oleic acid chloride at a 1:1 mole ratio at a temperature of about 80° C. with simple removal of the hydrogen chloride formed and recovery of sucrose monooleate. Similarly, sucrose monooleate can be obtained by heating a 1:1 mole mixture of methyl oleate and sucrose at a temperature of about 90° C. in the presence of a base catalyst, distilling the methanol formed and recovering the sucrose monooleate. While it is not important for the purposes of this invention, the sucrose monooleate formed in the foregoing manner is believed to be esterified predominantly at the hydroxyl group labeled (1) in the above formula. However, commercial grades of this material include, as minor components, compounds wherein the sucrose is esterified at hydroxyl groups (2) and (3) as well as even smaller amounts esterified at one or more of the other five ring hydroxyl groups. A similar situation obtains with the other sugar esters used herein. For example, raffinose, which can be considered to be a condensate of galactose and sucrose, can be esterified in the foregoing manner in any one of the ten hydroxyl groups and used herein. However, it is believed that the esterification of raffinose occurs predominantly at the —CH$_2$OH group on the galactose ring, with minor amounts of esterification also occurring at the —CH$_2$OH groups on the sucrose portion of the molecule. Accordingly, when esterified raffinose is used as a sugar ester herein, it comprises a mixture of these various esters. Such sugar esters mixtures are entirely suitable for use herein.

The following is a list of typical sugar esters suitable for use in the instant invention but is not intended to be limiting of such esters and is only mentioned by way of exemplification: glucose monooctanoate, glucose monocaprate, glucose monolaurate, glucose monomyristate, galactose monopalmitate, galactose monostearate, galactose monooleate, mannose mono-eicosanate, glucose dicaprate, glucose dilaurate, glucose dioleate, galactose dimyristate, galactose dioleate, mannose dipalmitate, xylose dioleate, xylose dioctanoate, xylose di-eicosanate, sucrose monooctanoate, sucrose monocaprate, sucrose monolaurate, sucrose monomyristate, sucrose monopalmitate, sucrose monostearate, sucrose monooleate, sucrose mono-eicosanate, sucrose dioctanoate, sucrose dicaprate, sucrose dilaurate, sucrose dimyristate, sucrose dipalmitate, sucrose distearate, sucrose dioleate, sucrose di-eicosanate, sucrose trioctanoate, sucrose tricaprate, sucrose trilaurate, sucrose trimyristate, sucrose tripalmitate, sucrose tristearate, sucrose trioleate, sucrose tri-eicosanate, maltose monooctanoate, maltose monocaprate, maltose monolaurate, maltose monomyristate, maltose monopalmitate, maltose monostearate, maltose monooleate, maltose mono-eicosanate, maltose dioctanoate, maltose dilaurate, maltose dioleate, cellibiose distearate, cellibiose dioleate, cellibiose di-eicosanate, galactose monooctanoate, galactose monocaprate, galactose monolaurate, galactose monomyristate, galactose monopalmitate, galactose monostearate, galactose monooleate, galactose mono-eicosanate, galactose dioctanoate, galactose dilaurate, galactose dimyristate, galactose dipalmitate, galactose distearate, galactose dioleate, galactose di-eicosanate, galactose trioctanoate, galactose trioleate, cellibiose tricaproate, cellibiose trilaurate, cellibiose trioleate, maltose tristearate, maltose trioleate, maltose tri-eicosanate, raffinose monooctanoate, raffinose monocaprate, raffinose monolaurate, raffinose monomyristate, raffinose monopalmitate, raffinose monostearate, raffinose monooleate, raffinose mono-eicosanate, raffinose dioctanoate, raffinose dioleate, raffinose trioleate, gentianose octanoate, gentianose monostearate, gentianose monooleate, gentianose mono-eicosanate, gentianose dioctanoate, gentianose dilaurate, gentianose dioleate, gentianose di-eicosanate, gentianose tricaprate, gentianose trilaurate and gentianose trioleate. Preferred sugar esters herein are sucrose monooctanoate, sucrose monodecanoate, sucrose monolaurate, sucrose monomyristate, sucrose monopalmitate, sucrose monostearate, sucrose monooleate and sucrose dioleate.

Other sugar esters suitable for use in the compositions of this invention are the alkyl polyoxyalkylene sugar esters wherein one hydroxyl group is substituted with a C$_8$–C$_{18}$ alkyl group and wherein one or more of the hydroxyl groups on the sugar molecule are replaced by an ester or ether substituent containing the moiety $-(CH_2)_xO]_y$ wherein x is an integer from 2 to about 4, preferably 2, and wherein y is an integer from about 1 to about 50, preferably 8 to 30, i.e., polyoxyalkylene substituents. Especially preferred herein are sugar esters wherein the polyoxyalkylene substituent is a polyoxyethylene substituent containing from about 8 to about 30 polyoxyethylene groups. Such materials wherein sorbitan is the sugar moiety are commercially available under the tradename "Tweens". Such mixed esters can be prepared by first acylating a sugar at a 1:1 mole ratio with a hydrocarbyl acid halide followed by reaction with the corresponding polyoxyalkylene acid halide or alkylene oxide to provide the desired material. The simple polyoxyalkylene esters of disaccharides, especially sucrose, wherein the polyoxyalkylene groups contain up to about 20 alkylene oxide moieties are another useful class of sugar esters herein. It is to be understood that the polyoxyalkylene derivatives of any of the sugars noted hereinabove are suitable for use as the sugar esters herein. The following list of typical polyoxyalkylene sugar derivatives and mixed polyoxyalkylene-acyl sugar esters suitable for use as the sugar ester component in the instant invention is not intended to be limiting of such esters and is mentioned by way of exemplification. The numeral following the polyoxyalkylene substituent denotes the number of repeating oxyalkylene groups in the polymer chain and is standard terminology for these kinds of materials. Suitable polyoxyalkylene sugar esters include sucrose monooleate polyoxyethylene (20); sucrose dipolyoxyethylene (30); fructose monopalmitate polyoxypropylene (10); galactose tri-polyoxybutylene (50); sucrose di-polyoxypropylene (15); sucrose monoeicosanate polyoxyethylene (20); sucrose dioleate polyoxyethylene (20); sorbitan monooleate polyoxyethylene (20); sorbitan monopalmitate polyoxyethylene (20); glucose monooctanoate diethyleneoxide (1); and glucose dioleate polyoxybutylene (20). Of the foregoing sugar esters, the sucrose monooleate polyoxyethylenes, especially the polyoxyethylene 10's, and the sorbitan monooleate polyoxyethylenes, especially the polyoxyethylene 10's, are preferred in the compositions herein.

The compositions herein also contain as an essential ingredient a compound selected from the group consisting of sulfoxides of the formula R$^1$S(O)R$^2$, wherein R$^1$ and R$^2$ are as defined hereinabove, and tertiary phosphine oxides of the formula R$^3$R$^4$R$^5$P(O) wherein R$^3$, R$^4$ and R$^5$ are as defined hereinabove. Preferred herein are the alkyl sulfoxides wherein R$^1$ is an alkyl or hydroxyalkyl substituent containing about 8 to about 12 carbon atoms and R$^2$ is a low molecular weight alkyl or low molecular weight hydroxyalkyl group containing about 1 to about 8 carbon atoms. Alkyl tertiary phosphine oxides wherein R$^3$ is an alkyl or hydroxyalkyl substituent containing 8 to 12 carbon atoms and R$^4$ and R$^5$ are each lower alkyl or lower hydroxyalkyl substituents are the preferred phosphine oxides herein.

Examples of lower alkyl and lower hydroxyalkyl substituents in the foregoing sulfoxide and phosphine oxides include, for example, methyl, ethyl, propyl, hydroxymethyl, 1-hydroxypropyl, etc. Substituted alkyl groups referred to in the sulfoxide and phosphine oxide definitions herein include alkoxyalkyl (e.g., methoxy) and ketoalkyl, for example; heteroalkyl groups include oxaalkyl, thiaalkyl, and azaalkyl, for example.

The alkyl sulfoxides suitable for use herein include those materials disclosed in U.S. Pat. No. 3,527,864 and U.S. Pat. No. 3,551,554, incorporated herein by reference. The most preferred alkyl sulfoxides for use herein have group R$^1$ as a hydroxycarbyl alkyl or hydroxyalkyl substituent containing from about 8 to about 12 carbon atoms, and $R^2$ as a low molecular weight hydrocarbyl alkyl substituent. If group $R^1$ of the alkyl sulfoxide contains less than about 8 carbon atoms, substantially higher concentrations than the 10% concentration specified herein must be employed to enhance penetration. For example, hexyl methyl sulfoxide must be used at a concentration of about 30% or more to significantly enhance penetration. The lower homologues must be used at solvent concentrations, e.g., 50% or more to accomplish this purpose. At these concentrations these lower sulfoxides (below $C_8$) can produce undesired systemic effects in some individuals. If $R^1$ contains substantially more than 12 carbon atoms, the sulfoxide will not be soluble enough to provide the desired degree of penetration enhancement.

Examples of $R^1$ suitable herein include octyl, nonyl, decyl, undecyl, dodecyl, 3-decenyl, 2-dodecenyl, 3-undecenyl, 3-octenyl, 2-ketooctyl, 2-ketodecyl, 2-ketoundecyl, 2-ketododecyl, 2-hydroxyoctyl, 2-hydroxydecyl, 2-hydroxyundecyl, 2-hydroxydodecyl, 3-hydroxyundecyl, 3-methoxyundecyl, 2-methoxydodecyl, 3,6-dioxadodecyl, 2-ethylhexyl, and branched chain nonyl and dodecyl resulting from polymerization of three and four moles of propylene, respectively. Examples of $R^2$ as lower alkyl include methyl, ethyl, propyl, butyl, hydroxymethyl, 2-hydroxyethyl, 3-hydroxypropyl, and 4-hydroxybutyl.

Especially preferred sulfoxides for the purposes of this invention are the dialkyl sulfoxides wherein $R^1$ is a hydrocarbyl alkyl or hydroxy-substituted alkyl group containing from 8 to 12 carbon atoms and $R^2$ is methyl, ethyl or propyl. As examples of these preferred sulfoxides there may be mentioned octyl methyl sulfoxide, nonyl methyl sulfoxide, decyl methyl sulfoxide, undecyl methyl sulfoxide, dodecyl methyl sulfoxide, 2-hydroxydecyl methyl sulfoxide, 2-hydroxyundecyl methyl sulfoxide and 2-hydroxydodecyl methyl sulfoxide. Decyl methyl sulfoxide is especially preferred.

The sulfoxide compounds disclosed herein can be used singly or in combination for the purpose of this invention. These compounds are readily obtainable by well known methods. For example, they can be prepared by the conventional method of first preparing the corresponding thioether and then oxidizing to the sulfoxide. The methods of carrying out these steps are reported in A. Schoberl and A. Wagner "Methoden Organischen Chemie", Houben-Weyl, 4th ed., Georg Thieme Verlog, Stuttgart, vol. IX, pp. 97–143, 211–218 (1955). Further methods for preparing sulfoxide compounds are disclosed in U.S. Pat. Nos. 3,288,858; 3,288,859; and 3,288,860, incorporated herein by reference.

The concentration of sulfoxide employed herein is at least about 0.1% by weight of the composition and can range from about 0.1% to about 10.0% by weight. If concentrations less than about 0.1% are used the degree of penetration enhancement attained, especially with the lower chain length sulfoxides (e.g., octyl methyl sulfoxide), is not appreciable. If concentrations greater than about 10.0% are employed, solubility problems may be encountered with the higher chain length sulfoxides (e.g., dodecyl isopropyl sulfoxide) and no substantial improvement in penetration is seen. Preferably, the concentration of sulfoxide will range from about 0.1% to about 1% by weight of the total composition.

As disclosed hereinabove, the tertiary phosphine oxides useful in the compositions of this invention are of the formula $R^3R^4R^5PO$. Examples of $R^3$ include methyl, ethyl, propyl, butyl, hexyl, heptyl, octyl, nonyl, decyl, undecyl, dodecyl, 2-propenyl, 3-decenyl, 2-dodecenyl, 3-undecenyl, 3-octenyl, 2-ketobutyl, 2-ketohexyl, 2-ketooctyl, 2-detodecyl, 2-ketoundecyl, 2-ketododecyl, 2-hydroxypropyl, 2-hydroxyhexyl, 3-hydroxyheptyl, 2-hydroxyoctyl, 2-hydroxydecyl, 2-hydroxyundecyl, 2-hydroxydodecyl, 3-hydroxyundecyl, 2-metoxybutyl, 3-methoxyundecyl, 2-methoxydodecyl, 2-chlorodecyl, 3-chlorobutyl, 2-thiomethylhexyl, 3,6-dioxadodecyl, 2-oxaheptyl, 3-azahexyl, 2-thiadecyl, 2-ethylhexyl, phenyl, naphthyl, m-tolyl, benzyl, and branched chain nonyl and dodecyl resulting from polymerization of three and four moles of propylene, respectively. If the $R^3$ group contains more than about 12 carbon atoms, it has been found that enhanced penetration does not occur.

Examples of $R^4$ and $R^5$ include methyl, ethyl, propyl, hydroxymethyl, 1-hydroxypropyl, 2-hydroxyethyl, and the like.

Especially preferred phosphine oxides for the purpose of this invention are those in which $R^3$ is a hydrocarbyl alkyl or hydroxy-substituted alkyl substituent containing from 8 to 12 carbon atoms and $R^4$ and $R^5$ are each methyl, ethyl or propyl. As examples of these preferred phosphine oxides there may be mentioned octyl dimethyl phosphine oxide, nonyl diethyl phosphine oxide, decyl dimethyl phosphine oxide, undecyl dimethyl phosphine oxide, dodecyl dimethyl phosphine oxide, 2-hydroxydecyl dimethyl phosphine oxide, 2-hydroxyundecyl dimethyl phosphine oxide and 2-hydroxydodecyl dimethyl phosphine oxide. Dodecyl dimethyl phosphine oxide is especially preferred.

The foregoing phosphine oxides can be used singly, in combination, or in combination with the foregoing sulfoxides, for the purpose of this invention. These compounds can be prepared by methods disclosed by D. Karrell Berlin and George B. Butler, "Chemical Reviews" 60 243–259 (1960). In general, the phosphine oxides are prepared by oxidizing the corresponding tertiary phosphine for example, with hydrogen peroxide. Further methods for preparing phosphine oxides suitable for use herein are disclosed in British Pat. Nos. 976,974 and 995,260, incorporated herein by reference.

The desired concentration of phosphine oxide employed herein depends largely on the chain length of $R^3$ and the type of composition involved, but preferably ranges from about 0.1% to about 10% by weight. If concentrations less than about 0.1% are used, the degree of penetration enhancement attained, especially with the lower chain length tertiary phosphine oxides (e.g., trimethyl phosphine oxide), is not appreciable. If concentrations of the higher chain length phosphine oxides (e.g., dodecyl diethyl phosphine oxide) greater than about 10% are employed, solubility problems may be encountered and no substantial improvement is seen using such higher concentrations. Preferably, the concentration of phosphine oxide containing an $R^3$ group having from 8 to 12 carbon atoms will range from about 1% to 8% by weight of the total composition. The suitable concentrations for the lower molecular weight phosphine oxides, e.g., wherein $R^3$ contains less than about 6 carbon atoms is from about 10% to 90% and preferably above 50%, e.g., solvent concentrations.

The compositions comprising the sugar ester and skin penetration enhancing agent disclosed herein are designed primarily for topical application to tissue and are preferably in a liquid or semi-liquid state. Accordingly, when solid sugar esters and/or sulfoxides or phosphine oxides are used to prepare the compositions herein, they are preferably formulated in combination with a pharmaceutically acceptable liquid carrier. It is desirable that the selected liquid carrier be capable of co-dissolving the sugar ester and sulfoxide or phosphine oxide. When a pharmacologically active agent is incorporated in the composition in the manner hereinafter detailed, it is desirable that the total composition be capable of co-dissolving this component.

Carrier materials suitable for use in the instant compositions include those well-known for use in the cosmetic and medical arts as bases for ointments, lotions, salves, aerosols, suppositories and the like. Suitable carriers include, for example, water, liquid alcohols, liquid glycols, liquid polyalkylene glycols, liquid esters, liquid amides, liquid protein hydrolysates, liquid alkylated protein hydrolysates, liquid lanolin and lanolin derivatives, and like materials commonly employed in cosmetic and medicinal compositions. Exemplary carriers herein include alcohols, including both monohydric and polyhydric alcohols, e.g., ethanol, isopropanol, glycerol, sorbitol, 2-methoxyethanol, diethyleneglycol, ethylene glycol, hexyleneglycol, mannitol, and propylene glycol; ethers such as diethyl or dipropyl ether; polyethylene glycols and methoxypolyoxyethylenes (carbowaxes having molecular weight ranging from 200 to 20,000); polyoxyethylene glycerols, polyoxyethylene sorbitols, and stearoyl diacetin. Oil-in-water emulsions such as cold cream bases can also be used.

Preferably, the carrier herein is a pharmaceutically acceptable liquid alcohol containing from about 2 to about 6 carbon atoms. Mixtures comprising from about 0% to 80% by weight of water and about 20% to 100% by weight of said $C_2$ to $C_6$ alcohols are also suitable. Suitable alcohols herein include ethanol, isopropanol, hexanol, and the like. Especially preferred carriers herein are water-ethanol (ethyl alcohol) mixtures at a weight ratio range of about 1:20 to 5:1. Ethanol containing from about 5% to about 50% by weight of water, especially 40:60 volume (i.e., 33.35% by weight) ethanol-water, is preferred as the carrier.

The compositions herein can also include various agents and ingredients commonly employed in dermatological and cosmetic ointments and lotions. For example, perfumes, thickening agents such as carboxymethylcellulose, coloring agents and the like can be present in the compositions to provide a more pleasing aesthetic aspect.

The following examples are intended to illustrate typical tissue penetration enhancing compositions of this invention but are not intended to be limiting thereof. All materials used in the compositions are commercially available, or can be prepared in the manner described hereinabove. The enhanced tissue penetration of the various pharmacologically active agents afforded by the compositions herein is measured by the techniques fully described in U.S. Pat. No. 3,527,864. Fluorescence microscopy of excised tissue is conveniently used to estimate tetracycline penetration.

EXAMPLE I

| Ingredient | Percent (By Weight) |
|---|---|
| Sucrose monooleate | 0.125 |
| Decyl methyl sulfoxide | 0.125 |
| Ethanol | 33.35 |

| Ingredient | Percent (By Weight) |
|---|---|
| Water | Balance |

The above ingredients are blended mechanically and provide a fluid ointment base adapted to topical application to skin and suitable for enhancing the penetration of all manner of pharmacologically active agents into and through animal tissue. For example, tetracycline hydrochloride (ca. 0.5%) is dissolved in the composition and is found to penetrate into animal skin to a substantially greater depth than when similarly applied in conjunction with ethanol-water, ethanol-water-decyl methyl sulfoxide, or ethanol-water-sucrose monooleate ointment bases.

In the above composition, the decyl methyl sulfoxide is replaced by an equivalent amount of octyl methyl sulfoxide, nonyl methyl sulfoxide, undecyl methyl sulfoxide, dodecyl methyl sulfoxide, 2-hydroxydecyl methyl sulfoxide, 2-hydroxyundecyl methyl sulfoxide, and 2-hydroxydodecyl methyl sulfoxide, respectively, and equivalent results are secured.

In the above composition, the sucrose monooleate is replaced by an equivalent amount of sucrose monolaurate, sucrose monomyristate, sucrose monopalmitate, sucrose monostearate, sucrose dipalmitate, sucrose dioleate, and sucrose monooleate polyoxyethylene (20), respectively, and equivalent results are secured.

EXAMPLE II

| Ingredient | Percent (By Weight) |
|---|---|
| Sucrose monooleate | 1.0 |
| Dodecyl dimethyl phosphine oxide | 10.0 |
| Isopropanol | 75.0 |
| Water | Balance |

The above ingredients are blended and provide a fluid ointment base suitable for enhancing the penetration of all manner of pharmacologically active agents into and through animal tissue. For example, tetracycline hydrochloride (ca. 0.5%) is dissolved in the composition and is found to penetrate into animal skin to a depth substantially greater than when similarly applied in conjunction with isopropanol-water, isopropanol-water-dodecyl dimethyl phosphine oxide or isopropanol-water-sucrose monooleate ointment bases.

In the above composition, the dodecyl dimethyl phosphine oxide is replaced by an equivalent amount of octyl dimethyl phosphine oxide, nonyl dimethyl phosphine oxide, decyl dimethyl phosphine oxide, undecyl dimethyl phosphine oxide, 2-hydroxydecyl dimethyl phosphine oxide, 2-hydroxyundecyl dimethyl phosphine oxide, and 2-hydroxydodecyl dimethyl phosphine oxide, respectively, and equivalent results are secured.

In the above composition, the sucrose monooleate is replaced by an equivalent amount of sucrose monolaurate, sucrose monomyristate, sucrose monopalmitate, sucrose monostearate, sucrose dipalmitate, sucrose dioleate, and sucrose monooctanoate, and sucrose monodecanoate, respectively, and equivalent results are secured.

EXAMPLE III

| Ingredient | Percent (By Weight) |
| --- | --- |
| Sucrose monooleate | 0.1 |
| Decyl methyl sulfoxide | 0.25 |
| Carboxymethylcellulose | 1.0 |
| Glycerol | 15.0 |
| Ethanol | 50.0 |
| Water | Balance |

The above composition provides a creamy ointment base adapted to topical application to skin and is suitable for enhancing the penetration of all manner of pharmacologically active agents into and through animal tissue. For example, triamcinolone acetonide (ca. 0.1%) is dissolved in the composition and is found to penetrate into animal skin to a substantially greater depth than when similarly applied in conjunction with ethanol-water, ethanol-water-glycerol, ethanol-water-glycerol-decyl methyl sulfoxide, or ethanol-water-glycerol-sucrose monooleate cream bases.

In the above composition, the ethanol is replaced by an equivalent amount of isopropanol and 1-hexanol, respectively, with equivalent results.

A tacky, substantially anhydrous composition is prepared by deleting the water and ethanol in the composition of Example III. The resulting tacky composition is adapted to application to animal skin and is especially suited for use when removal of the composition by perspiration is desirably avoided. The anhydrous composition promotes the penetration of all manner of pharmacologically active agents into and through the skin.

From the foregoing, it is seen that the compositions herein are especially adapted to topical application to animal tissue to enhance the penetration of various pharmacologically active agents. In general, preferred compositions for this purpose comprise from about 0.1% to about 1.0% by weight of sucrose monooleate from about 0.1% to about 1% by weight of decyl methyl sulfoxide from about 20% to about 70% by weight of water and from about 20% to about 70% by weight of ethyl alcohol. The following is intended to illustrate the broad range of pharmacologically active agents which can be employed in conjunction with the foregoing compositions and to illustrate that such compositions promote the penetration of a wide variety of pharmacologically active agents into and through animal tissue.

One class of pharmacologically active agents suitable for use in conjunction with the tissue penetration compositions herein are the antimicrobials. As used herein, the term "antimicrobials" includes both the antibiotics such as the penicillins, tetracyclines, aureomycins, streptomycins, and griseofulvins, as well as the synthetically produced antimicrobial agents such as the phenols, the various chlorinated phenolics, chlorinated aromatics and carbanilides, quaternary ammonium compounds, bis-biguanides and the like. Preferably, the antimicrobial agents used herein are soluble in the tissue penetration composition. Since the compositions herein usually contain a proportion of water, alcohol, or water-alcohol mixtures, as hereinabove described, the antimicrobial agents can be those which are soluble in water, alcohol, or water-alcohol mixtures.

Exemplary antimicrobial agents suitable for use herein include the tetracyclines as well as the salts thereof, for example, tetracycline hydrochloride and the tetracycline phosphate complex marketed under the trademarks "Tetrex" and "Panmycin Phosphate", and the like. Tetracycline analogs, e.g., the oxytetracyclines or terramycins, e.g., terramycin hydrochloride, terramycin disodium salt dihydrate, and the like are also suitable herein. The gramicidins, including gramicidin D and gramicidin S, can be used as the antimicrobial agent herein. Aureothricin, aureomycin, tyrothricin, and any of the penicillins, e.g., penicillin AT, penicillin BT, penicillin S potassium, penicillin V, and the like, are also useful as the antimicrobial agent. From the foregoing, it can be seen that a wide variety of naturally-occurring antibiotic substances can be employed as the penetrant in the instant compositions. In each instance, the compositions herein enhance the penetration of the foregoing antimicrobial agents into and through animal tissue.

Other suitable antimicrobial agents herein include the synthetically-produced organic compounds recognized as having antimicrobial properties. For example, the well-known quaternary ammonium salts, e.g., cetylpyridinium chloride, dodecyltrimethylammonium bromide, decylmorpholinium sulfate, and the like, are suitable for use as the antimicrobial agent herein. Likewise, halogenated antibacterial agents such as 3,5,4'-tribromosalicylanilide, bis-(3,5,6-trichloro-2-hydroxyphenyl)methane, bis-(3,5-dichloro-2-hydroxyphenyl)-sulfide, 3-trifluoromethyl-4,4'-dichlorocarbanilide, and mixtures thereof, can be used in conjunction with the compositions herein to enhance their penetration into and through animal tissue. Another class of antimicrobial agents are the well-known alkyl or aryl bis-biguanide compounds. Such materials are commercially available. Also suitable herein are the salts, e.g., acetate, gluconate, hydrochloride, etc., of the foregoing bis-biguanides. Exemplary bis-biguanides suitable for use herein are 1,1'-hexamethylenebis[5'-(p-chlorophenyl)]-biguanide and the acetate and gluconate salts thereof, and 1,1'-hexamethylenebis[5-(2-ethylhexyl)]-biguanide and the acetate and gluconate salts thereof. A number of other suitable synthetic anti-bacterial agents are described in U.S. Pat. No. 3,281,366 to Judge, et al., incorporated herein by reference.

Preferred antimicrobial agents for use herein include tetracycline, tetracycline hydrochloride, equilibrium mixtures of epi-tetracycline hydrochloride and tetracycline hydrochloride (formed on dissolution of tetracycline hydrochloride in water), 3,5,4'-tribromosalicylanilide, bis-(3,5,6-trichloro-2-hydroxyphenyl)methane, bis-(3,5-dichloro-2-hydroxyphenyl)sulfide, 3-trifluoromethyl-4,4'-dichlorocarbanilide, 1,1'-hexamethylenebis[5'-(p-chlorophenyl)]biguanide, 1,1'-hexamethylenebis[5'-(2-ethylhexyl)]biguanide, cetylpyridinium chloride, zinc undecylenate, oxytetracycline, terramycin, gramicidin, aureomycin, neomycin, tyrothricin, sulfonilamide, penicillin and zinc pyridinethione-1-oxide. Especially preferred antimicrobial agents herein include tetracycline hydrochloride and the equilibrium mixture of tetracycline hydrochloride and epi-tetracycline hydrochloride which forms spontaneously after aqueous solutions of tetracycline hydrochloride have been allowed to age at about 90° F. for about 28 days. In general, this equilibrium mixture comprises about 40%–45% (wt.) tetracycline hydrochloride and 55%–60% (wt.) epi-tetracycline hydrochloride.

The following examples are intended to illustrate the tissue penetration enhancing compositions of this invention containing as the pharmacologically active component from about 0.005% to about 10% by weight of an antimicrobial agent.

EXAMPLE IV

| Ingredient | Percent (By Weight) |
|---|---|
| Sucrose monooleate | 0.125 |
| Tetracycline hydrochloride | 0.5 |
| Decyl methyl sulfoxide | 0.125 |
| Ethanol | 33.35 |
| Water | Balance |

The above composition is applied to animal skin and results in a substantial increase in the depth of penetration of the tetracycline hydrochloride over similar compositions without the sucrose monooleate.

The above composition is spread onto human skin affected with acne twice daily for about two weeks (28 total applications; about 2 oz. total product used). The treatment results in a substantial remission of acne lesions and a marked decrease in skin inflammation. The remission of acne symptoms is significantly better than with equivalent treatments using compositions which do not contain the sugar ester. Treatment is continued ad libitum and the skin remains substantially free from acne lesions and inflammation of the sebaceous glands. Surprisingly, a decreased number of "blackheads" is also noted.

In the above composition, the tetracycline hydrochloride is replaced by an equivalent amount of an equilibrium mixture of tetracycline hydrochloride and epi-tetracycline hydrochloride formed by dissolving tetracycline hydrochloride in water and allowing the solution to stand at about 90° F. for about 28 days (equilibrium mix; ca. 40–45% tetracycline hydrochloride, 55–60% epi-tetracycline hydrochloride). Equivalent skin penetration enhancement and anti-acne benefits are secured.

The composition of Example IV is modified by the addition of 0.1% by weight of sodium bisulfite and the color stability on prolonged storage is substantially increased.

In the above composition, the decyl methyl sulfoxide is replaced by an equivalent amount of octyl methyl sulfoxide, nonyl methyl sulfoxide, undecyl methyl sulfoxide, dodecyl methyl sulfoxide, 2-hydroxydecyl methyl sulfoxide, 2-hydroxyundecyl methyl sulfoxide, and 2-hydroxydodecyl methyl sulfoxide, respectively, and equivalent results are secured.

In the above composition, the sucrose monooleate is replaced by an equivalent amount of sucrose monooctanoate, sucrose monolaurate, sucrose monomyristate, sucrose monopalmitate, sucrose monostearate, sucrose monodecanoate, sucrose dioleate, sucrose di-polyoxypropylene (10), glucose dioleate polyoxyethylene (20) and sucrose palmitate polyoxyethylene (20), respectively, and equivalent results are secured.

In the above composition the ethanol-water mixture is replaced by an equivalent amount of ethanol, 95% ethanol-5% water, isopropanol, 1:1 isopropanol-water and 1:1 hexanol-water mixtures, respectively, and equivalent results are secured.

EXAMPLE V

| Ingredient | Percent (By Weight) |
|---|---|
| Sucrose monooleate | 0.25 |
| Colistin | 0.25 |
| Decyl methyl sulfoxide | 0.25 |
| Ethanol | 15.0 |
| Lanolin | 25 |
| Water | Balance |

The above composition is applied to animal skin and results in a substantial increase in the depth of penetration of the colistin into the skin over similar compositions without the sucrose monooleate.

The above composition is useful for the treatment of first and second degree burns, inasmuch as the lanolin provides a soothing emollient effect while the colistin penetrates into the burn area to combat bacterial infection.

In the above composition, the colistin is replaced by an equivalent amount of penicillin, tetracycline, tetracycline hydrochloride, an equilibrium mixture of tetracycline hydrochloride and epi-tetracycline hydrochloride, 3,5,4'-tribromosalicyanilide, bis-(3,5,6-trichloro-2-hydroxyphenyl)methane, bis-(3,5-dichloro-2-hydroxyphenyl)sulfide, 3-trifluoromethyl-4,4'-dichlorocarbanilide, 1,1'-hexamethylene bis[5'-(p-chlorophenyl)]biguanide, 1,1'-hexamethylene bis[5'-(2-ethylhexyl)]biguanide, cetylpyridinium chloride, zinc undecylenate, oxytetracycline, terramycin, gramicidin, aureomycin, neomycin, tyrothricin, sulfonilamide, and zinc pyridinethione-1-oxide, respectively, and equivalent results are secured.

The above composition is formulated with the addition of 0.75% by weight of benzocaine. The penetration of the benzocaine into the burn area is promoted by the base composition and provides a soothing anesthetic benefit to the user.

The foregoing composition is formulated using an equivalent amount of octyl dimethyl phosphine oxide, nonyl dimethyl phosphine oxide, decyl dimethyl phosphine oxide, undecyl dimethyl phosphine oxide, dodecyl dimethyl phosphine oxide, 2-hydroxydecyl dimethyl phosphine oxide, 2-hydroxyundecyl dimethyl phosphine oxide, and 2-hydroxydodecyl dimethyl phosphine oxide, respectively, in place of the decyl methyl sulfoxide and equivalent results are secured.

The sucrose monooleate is replaced by an equivalent amount of sucrose dioleate, sucrose dipalmitate, glucose monooctanoate, galactose mono-eicosanate, xylose dioleate, sucrose mono-eicosanate, sucrose di-eicosanate, maltose monopalmitate, cellibiose distearate, galactose tripalmitate, raffinose monocaprate, gentianose trieicosanate, and gentianose trioleate, respectively, and equivalent results are secured.

Preferred antimicrobial compositions prepared in accordance with this invention comprise:
(1) from about 0.1% to about 1% by weight of sucrose monooleate;
(2) from about 0.1% to about 8% by weight of decyl methyl sulfoxide;
(3) from about 30% to about 70% by weight of water;
(4) from about 30% to about 70% by weight of ethyl alcohol; and
(5) from about 0.1% to about 1.0% by weight of a member selected from the group consisting of tetracycline hydrochloride and an equilibrium mixture of tetracycline hydrochloride and epi-tetracycline hydrochloride.

The following examples are intended to illustrate the tissue penetration enhancing compositions of this invention containing as the pharmacologically active component from about 0.1% to about 15% by weight of a topical anesthetic agent.

EXAMPLE VI

| Ingredient | Percent (By Weight) |
|---|---|
| Sucrose monooleate | 0.15 |
| Decyl methyl sulfoxide | 0.15 |
| Benzocaine | 1.0 |
| Ethanol (95%) | 50 |
| 1:1 mixture of dichlorodifluoromethane and chlorotrifluoromethane (propellant) | Balance |

The above composition is prepared in a pressurized can and is sprayed onto skin to provide a local anesthetic effect. The penetration of the benzocaine into and through the skin and dermal tissue is significantly enhanced by use of the sucrose monooleate-decyl methyl sulfoxide composition over compositions containing the decyl methyl sulfoxide or sucrose monooleate, alone. The enhanced penetration accounts for the improved anesthetic affect noted.

In the above composition, the benzocaine is replaced by an equivalent amount of procaine hydrochloride, nupercaine and pontocaine, respectively, and equivalent results are secured.

In the above composition, the decyl methyl sulfoxide is replaced by an equivalent amount of octyl methyl sulfoxide, nonyl methyl sulfoxide, undecyl methyl sulfoxide, dodecyl methyl sulfoxide, 2-hydroxydecyl methyl sulfoxide, 2-hydroxyundecyl methyl sulfoxide, 2-hydroxydodecyl methyl sulfoxide, octyl dimethyl phosphine oxide, nonyl dimethyl phosphine oxide, decyl dimethyl phosphine oxide, undecyl dimethyl phosphine oxide, dodecyl dimethyl phosphine oxide, 2-hydroxydecyl dimethyl phosphine oxide, 2-hydroxyundecyl dimethyl phosphine oxide, and 2-hydroxydodecyl dimethyl phosphine oxide, respectively, and equivalent results are secured.

In the foregoing composition, the sucrose monooleate is replaced by an equivalent amount of sucrose monooctanoate, sucrose monolaurate, sucrose monomyristate, sucrose monopalmitate, sucrose monostearate, sucrose dipalmitate, and sucrose dioleate, respectively, and equivalent results are secured.

Preferred anesthetic compositions herein comprise:
(1) from about 0.1% to about 1% by weight of sucrose monooleate;
(2) from about 0.1% to about 10% by weight of decyl methyl sulfoxide;
(3) from about 30% to about 70% by weight of water;
(4) from about 30% to about 70% by weight of ethyl alcohol; and
(5) from about 0.1% to about 5% by weight of a member selected from the group consisting of benzocaine, procaine hydrochloride, nupercaine and pontocaine.

The following examples are intended to illustrate the tissue penetration enhancing compositions of this invention containing as the pharmacologically active agent from about 0.1% to about 20% by weight of various organic sunscreens (i.e., agents which absorb ultraviolet light).

EXAMPLE VII

| Ingredient | Percent (By Weight) |
|---|---|
| Sucrose monooleate | 1.0 |
| Decyl methyl sulfoxide | 1.0 |
| p-Aminobenzoic acid | 5.0 |
| Dimethylsilicone fluid (mol. wt. 2500) | 5.0 |
| Ethanol (95%) | Balance |

The above composition is prepared by simple blending and is applied to skin to provide a sunscreen effect. The penetration of the p-aminobenzoic acid into the skin is significantly enhanced by use of the sucrose monooleate-decyl methyl sulfoxide composition over compositions containing the decyl methyl sulfoxide or sucrose monooleate alone. The enhanced penetration provides increased sunscreening benefits inasmuch as the p-aminobenzoic acid is not readily removed by moisture or perspiration.

In the above composition, the p-aminobenzoic acid is replaced by an equivalent amount of homomenthyl salicylate, isopropyl cinnamate, p-methoxycinnamic acid, 2-ethylhexyl salicylate, dipropyleneglycol salicylate, monoglyceryl, p-aminobenzoate, digalloyl trioleate, menthyl anthranilate, and mixtures thereof, and equivalent results are secured.

In the above composition, the decyl methyl sulfoxide is replaced by an equivalent amount of octyl methyl sulfoxide, nonyl methyl sulfoxide, undecyl methyl sulfoxide, dodecyl methyl sulfoxide, 2-hydroxydecyl methyl sulfoxide, 2-hydroxyundecyl methyl sulfoxide, 2-hydroxydodecyl methyl sulfoxide, octyl dimethyl phosphine oxide, nonyl dimethyl phosphine oxide, decyl dimethyl phosphine oxide, undecyl dimethyl phosphine oxide, dodecyl dimethyl phosphine oxide, 2-hydroxydecyl dimethyl phosphine oxide, 2-hydroxyundecyl dimethyl phosphine oxide, and 2-hydroxydodecyl dimethyl phosphine oxide, respectively, and equivalent results are secured.

In the foregoing composition, the sucrose monooleate is replaced by an equivalent amount of sucrose monooctanoate, sucrose monolaurate, sucrose monomyristate, sucrose monopalmitate, sucrose monostearate, sucrose dipalmitate, and sucrose dioleate, respectively, and equivalent results are secured.

Preferred sunscreen compositions herein comprise:
(1) from about 0.1% to about 1% by weight of sucrose monooleate;
(2) from about 0.1% to about 10% by weight of decyl methyl sulfoxide;
(3) from about 30% to about 70% by weight of water;
(4) from about 30% to about 70% by weight of ethyl alcohol; and
(5) from about 0.5% to about 10% by weight of a member selected from the group consisting of p-aminobenzoic acid, homomenthyl salicylate, isopropyl cinnamate, p-methoxycinnamic acid, 2-ethylhexyl salicylate, dipropyleneglycol salicylate, monoglyceryl p-aminobenzoate, digalloyltrioleate and menthyl anthranilate.

The following examples are intended to illustrate the tissue penetration enhancing compositions of this invention containing from about 0.025% to about 2.5% by weight of various steroids as the pharmacologically active agent, said compositions being suitable for use as anti-inflammatories. The relative amounts of the steroid or steroid derivative used is determined on the basis of the relative physiological activities of these materials.

EXAMPLE VIII

| Ingredient | Percent (By Weight) |
| --- | --- |
| Sucrose monooleate | 0.5 |
| Decyl methyl sulfoxide | 0.25 |
| Triamcinolone acetonide | 0.1 |
| Ethanol-water (30:70 wt.) | Balance |

The above composition is prepared as a fluid cream and is applied to skin to provide a local anti-inflammatory effect. The penetration of the triamcinolone acetonide into and through the skin and dermal tissue is significantly enhanced by use of the sucrose monooleate-decyl methyl sulfoxide composition over compositions containing the decyl methyl sulfoxide or sucrose monooleate alone. The enhanced penetration accounts for the improved anti-inflammatory effect noted.

In the above composition, the triamcinolone acetonide is replaced by an equivalent amount of triamcinolone, fluocinolone acetonide, fluocinolone acetonide acetate, betamethasone 17-valerate, and by 2.5% by weight concentrations of cortisone and hydrocortisone acetate, respectively, and equivalent results are secured.

In the above composition, the decyl methyl sulfoxide is replaced by an equivalent amount of octyl methyl sulfoxide, nonyl methyl sulfoxide, undecyl methyl sulfoxide, dodecyl methyl sulfoxide, 2-hydroxydecyl methyl sulfoxide, 2-hydroxyundecyl methyl sulfoxide, 2-hydroxydodecyl methyl sulfoxide, octyl dimethyl phosphine oxide, nonyl dimethyl phosphine oxide, decyl dimethyl phosphine oxide, undecyl dimethyl phosphine oxide, dodecyl dimethylphosphine oxide, 2-hydroxydecyl dimethyl phosphine oxide, 2-hydroxyundecyl dimethyl phosphine oxide, and 2-hydroxydodecyl dimethyl phosphine oxide, respectively, and equivalent results are secured.

In the foregoing composition, the sucrose monooleate is replaced by an equivalent amount of sucrose monooctanoate, sucrose monolaurate, sucrose monomyristate, sucrose monopalmitate, sucrose monostearate, sucrose dipalmitate, sucrose dioleate and sorbitan monooleate polyoxyethylene (20), respectively, and equivalent results are secured.

Preferred steroid-containing compositions herein comprise:
 (1) from about 0.1% to about 1% by weight of sucrose monooleate;
 (2) from about 0.1% to about 10% by weight of decyl methyl sulfoxide;
 (3) from about 30% to about 70% of water; and
 (4) from about 30% to about 70% by weight of ethyl alcohol; and
 (5) from about 0.05% to about 2.5% by weight of a steroid selected from the group consisting of triamcinolone acetonide, hydrocortisone acetate, triamcinolone, cortisone, fluocinolone acetonide, fluocinolone acetonide acetate and betamethasone 17-valerate.

The foregoing steroid-containing compositions are additionally suited for the alleviation of psoriasis, eczema and eczema-like skin disorders.

The following examples describe the tissue penetration enhancing compositions herein and their use in conjunction with from about 0.5% to about 15% by weight of various astringent metal salts as antiperspirants.

EXAMPLE IX

| Ingredient | Percent (By Weight) |
| --- | --- |
| Sucrose monooleate | 0.1 |
| Decyl methyl sulfoxide | 2.0 |
| Aluminum chlorhydrate | 5.0 |
| Ethanol (95%) | 40 |
| 1:1 mixture of dichlorodifluoromethane and chlorotrifluoromethane (propellant) | Balance |

The above composition is prepared in a pressurized can and is sprayed onto skin to provide a local anti-perspirant effect. The penetration of the aluminum chlorhydrate into and through the skin and dermal tissue is significantly enhanced by use of the sucrose monooleatedecyl methyl sulfoxide compositions over compositions containing the decyl methyl sulfoxide or sucrose monooleate alone. The antiperspirant effectiveness of the compositions is assessed using the "forearm test" fully described in U.S. Pat. No. 3,527,864, above. The enhanced penetration accounts for the improved anti-perspirant effect noted.

In the above composition, the aluminum chlorhydrate is replaced by an equivalent amount of zirconium oxychloride, zinc chloride, aluminum tribromide, aluminum chloride ethanolate, and a 1:1 weight mixture of zirconium oxychloride and aluminum chlorhydrate, respectively, and equivalent results are secured.

In the above composition, the decyl methyl sulfoxide, is replaced by an equivalent amount of octyl methyl sulfoxide, nonyl methyl sulfoxide, undecyl methyl sulfoxide, dodecyl methyl sulfoxide, 2-hydroxydecyl methyl sulfoxide, 2-hydroxydecylmethyl sulfoxide, 2-hydroxydodecyl methyl sulfoxide, octyl dimethyl phosphine oxide, nonyl dimethyl phosphine oxide, decyl dimethyl phosphine oxide, undecyl dimethyl phosphine oxide, dodecyl dimethyl phosphine oxide, 2-hydroxydecyl dimethyl phosphine oxide, 2-hydroxyundecyl dimethyl phosphine oxide, and 2-hydroxydodecyl dimethyl phosphine oxide, respectively, and equivalent results are secured.

In the foregoing composition, the sucrose monooleate is replaced by an equivalent amount of sucrose monooctanoate, sucrose monolaurate, sucrose monomyristate, sucrose monopalmitate, sucrose monostearate, sucrose dipalmitate, and sucrose dioleate, respectively, and equivalent results are secured.

Preferred antiperspirant compositions herein comprise:
 (1) from about 0.1% to about 1% by weight of sucrose monooleate;
 (2) from about 0.1% to about 10% by weight of decyl methyl sulfoxide;
 (3) from about 50% to about 90% by weight of ethyl alcohol; and (4) from about 1% to about 10% by weight of an astringent metal salt selected from the group consisting of aluminum chlorhydrate, zirconium oxychloride and mixtures thereof.

The following examples describe compositions comprising the sugar ester, skin penetration enhancing agent and, as the pharmacologically active agent, various anti-metabolites useful in the treatment of psoriasis.

EXAMPLE X

| Ingredient | Percent (By Weight) |
| --- | --- |
| Sucrose monooleate | 1.0 |
| Decyl methyl sulfoxide | 1.0 |
| Methotrexate | 2.0 |
| Ethanol | 25.0 |
| Water | Balance |

The above composition is admixed by simple blending and is applied to skin. The penetration of the Methotrexate into and through the skin and dermal tissue is significantly enhanced by use of the sucrose monooleate-decyl methyl sulfoxide composition over compositions containing the decylmethyl sulfoxide or sucrose monooleate alone. The enhanced penetration provides improved anti-psoriasis benefits.

In the above compositions the Methotrexate is replaced by an equivalent amount of 5-methyldeoxycytidine, puromycin, arabinosyl cytosine, hydroxyurea and theophylline, respectively, with equivalent results.

In the above composition, the decyl methyl sulfoxide is replaced by an equivalent amount of octyl methyl sulfoxide, nonyl methyl sulfoxide, undecyl methyl sulfoxide, dodecyl methyl sulfoxide, 2-hydroxydecyl methyl sulfoxide, 2-hydroxyundecyl methyl sulfoxide, 2-hydroxyundecyl methyl sulfoxide, octyl dimethyl phosphine oxide, nonyl dimethyl phosphine oxide, decyl dimethyl phosphine oxide, undecyl dimethyl phosphine oxide, dodecyl dimethyl phosphine oxide, 2-hydroxydecyl dimethyl phosphine oxide, 2-hydroxyundecyl dimethyl phosphine oxide, and 2-hydroxydodecyl dimethyl phosphine oxide, respectively, and equivalent results are secured.

In the foregoing composition, the sucrose monooleate is replaced by an equivalent amount of sucrose monooctanoate, sucrose monolaurate, sucrose monomyristate, sucrose monopalmitate, sucrose monostearate, sucrose dipalmitate, and sucrose dioleate, respectively, and equivalent results are secured.

Preferred antimetabolite compositions herein comprise:
(1) from about 0.1% to about 1% by weight of sucrose monooleate;
(2) from about 0.1% to about 10% by weight of decyl methyl sulfoxide;
(3) from about 30% to about 70% by weight of water;
(4) from about 30% to about 70% by weight of ethyl alcohol; and
(5) from about 0.1% to about 10% by weight of a member selected from the group consisting of Methotrexate, 5-methyldeoxycytidine, puromycin, arabinosyl cytosine, and hydroxyurea.

The following examples describe compositions comprising the sugar ester, skin penetration enhancing agent and, as the pharmacologically active agent, from about 0.01% to about 10% by weight of Vitamin A or commercial preparations containing at least about 10,000 units of Vitamin A activity per gram.

EXAMPLE XI

| Ingredient | Percent (By Weight) |
| --- | --- |
| Sucrose monooleate | 1.0 |
| Decyl methyl sulfoxide | 1.0 |
| Vitamin A | 1.0 |
| Sorbitan Monooleate Polyoxyethylene (Emulsifier) | 2.0 |
| Lanolin | 5.0 |
| Water | Balance |

The above composition is applied to skin to provide anti-acne benefits. The penetration of the Vitamin A into and through the skin and dermal tissue is significantly enhanced by use of the sucrose monooleate-decyl methyl sulfoxide composition over compositions containing the decyl methyl sulfoxide or sucrose monooleate alone.

In the above composition, the decyl methyl sulfoxide is replaced by an equivalent amount of octyl methyl sulfoxide, nonyl methyl sulfoxide, undecyl methyl sulfoxide, dodecyl methyl sulfoxide, 2-hydroxydecyl methyl sulfoxide, 2-hydroxyundecyl methyl sulfoxide, 2-hydroxydodecyl methyl sulfoxide, octyl dimethyl phosphine oxide, nonyl dimethyl phosphine oxide, decyl dimethyl phosphine oxide, undecyl dimethyl phosphine oxide, dodecyl dimethyl phosphine oxide, 2-hydroxydecyl dimethyl phosphine oxide, 2-hydroxyundecyl dimethyl phosphine oxide, and 2-hydroxydodecyl dimethyl phosphine oxide, respectively, and equivalent results are secured.

In the foregoing composition, the sucrose monooleate is replaced by an equivalent amount of sucrose monooctanoate, sucrose monolaurate, sucrose monomyristate, sucrose monopalmitate, sucrose monostearate, sucrose dipalmitate, and sucrose dioleate, respectively, and equivalent results are secured.

Preferred vitamin compositions herein comprise:
(1) from about 0.1% to about 1% by weight of sucrose monooleate;
(2) from about 0.1% to about 10% by weight of decyl methyl sulfoxide;
(3) from about 30% to about 70% by weight of water;
(4) from about 30% to about 70% by weight of ethyl alcohol; and
(5) from about 0.1% to about 2% by weight of Vitamin A.

The following examples describe compositions comprising the sugar ester, skin penetration enhancing agent and, as the pharmacologically active agent, from about 0.1% to about 10% by weight of various natural oils well-known for their rubifacient and analgesic activity and ability to aid in the relief of muscular strain.

EXAMPLE XII

| Ingredient | Percent (By Weight) |
| --- | --- |
| Sucrose monooleate | 1.0 |
| Decyl methyl sulfoxide | 1.0 |
| Oil of Wintergreen | 2.0 |
| Hexanol | Balance |

The above composition is prepared by blending and is applied to skin to alleviate the discomforts of simple muscular strain. The penetration of the oil of wintergreen into and through the skin and muscular tissue is significantly enhanced by use of the sucrose monooleatedecyl methyl sulfoxide composition over compositions containing the decyl methyl sulfoxide or sucrose monooleate alone.

In the above composition, the oil of wintergreen is replaced by an equivalent amount of tincture of camphor, clove oil, and mixtures thereof, respectively, and equivalent results are secured.

The composition is formulated with the addition of about 0.01% by weight of cantharidin and provides an effective medication for treating mange in dogs and cattle.

In the above composition, the decyl methyl sulfoxide is replaced by an equivalent amount of 2-ketooctyl methyl sulfoxide, 3-methoxyundecyl methyl sulfoxide, 3,6-dioxadodecyl methyl sulfoxide, 3-octenyl hydroxymethyl sulfoxide, 2-hydroxyoctyl methyl sulfoxide, bis-(2-hydroxyoctyl)sulfoxide, 2-hydroxydodecyl hydroxymethyl sulfoxide, trimethyl phosphine oxide, phenyl dimethyl phosphine oxide, naphthyl ethyl hydroxymethyl phosphine oxide, 2-propenyl diethyl phosphine oxide, 2-ketobutyl diethanol phosphine oxide, 2-methoxybutyl methyl ethyl phosphine oxide, 2-chlorodecyl dimethyl phosphine oxide, 2-oxaheptyl dimethyl phosphine oxide, 3-azahexyl dimethyl phosphine oxide, phenyl dimethyl phosphine oxide and methyl dibenzyl phosphine oxide, respectively, and equivalent results are secured.

In the foregoing composition, the sucrose monooleate is replaced by an equivalent amount of sucrose monooctanoate, sucrose monolaurate, sucrose monomyristate, sucrose monopalmitate, sucrose monostearate, sucrose dipalmitate, and sucrose dioleate, respectively, and equivalent results are secured.

Preferred rubifacient compositions herein comprise:
(1) from about 0.1% to about 1% by weight of sucrose monooleate;
(2) from about 0.1% to about 10% by weight of decyl methyl sulfoxide;
(3) from about 30% to about 70% by weight of water;
(4) from about 30% to about 70% by weight of ethyl alcohol; and
(5) from about 0.1% to about 5% by weight of a member selected from the group consisting of oil of wintergreen, tincture of camphor, and mixtures thereof.

From the foregoing it is seen that the compositions herein enhance the penetration of a wide variety of pharmacologically active chemical substances into and through animal tissue. Furthermore, it is recognized that the compositions herein containing the various pharmacologically active agents are especially adapted to treatment of various disease conditions in humans and in animals by topical application thereto. The proportions of pharmacologically active agents disclosed in the examples are merely for the purposes of illustration inasmuch as these proportions can be varied depending on the type of agent being used, the relative severity of the disease condition, the rate of application by the user and the like.

It is further recognized that combinations of one, or more, pharmacological agents can be used conjointly with the penetration-enhancing compositions herein. For example, the conjoint use of steroidal anti-inflammatory materials with antimicrobial and anti-fungal agents is an art-recognized method for obtaining an improved anti-inflammatory response with inflamed tissue. The following example illustrates such a composition comprising a steroid-antimicrobial-antifungal composition in combination with the penetration-enhancing base of this invention.

EXAMPLE XIII

| Ingredient | Percent (By Weight) |
| --- | --- |
| Sucrose monooleate | 1.0 |
| Decyl methyl sulfoxide | 0.15 |
| Triamcinolone acetonide | 0.05 |
| Neomycin sulfate | 0.20 |
| Gramicidin | 0.05 |
| Ethanol-water (1:1) | Balance |

The above composition is prepared by blending the respective ingredients and is applied to skin to alleviate inflammation and the symptoms of eczema. The penetration of the triamcinolone acetonide, neomycin sulfate and gramicidin into the skin is significantly enhanced by the use of the sucrose monooleate-decyl methyl sulfoxide composition over compositions containing the decyl methyl sulfoxide or sucrose monooleate, alone.

In the above composition, the gramicidin is replaced by an equivalent amount of bacitracin and equivalent results are secured.

In the above composition, the decyl methyl sulfoxide is replaced by an equivalent amount of 3-octenyl methyl sulfoxide, 2-hydroxydecyl 2-hydroxyethyl sulfoxide, 2-hydroxydecyl bis-(hydroxymethyl)phosphine oxide, and tris-(hydroxymethyl)phosphine oxide, respectively, and equivalent results are secured.

In the above composition, the sucrose monooleate is replaced by an equivalent amount of fructose monopalmitate polyoxyethylene (20), galactose tri-polyoxybutylene (50) and sucrose di-polyoxypropylene (20), respectively, and equivalent results are secured.

It is also recognized that the invention encompasses as a method aspect a process for enhancing the penetration of pharmacologically active agents into and through animal tissue, especially skin, comprising applying said pharmacologically active agent topically to said tissue in combination with a sugar ester and a sulfoxide or phosphine oxide of the type disclosed herein. Sucrose monooleate and decyl methyl sulfoxide at proportions of sulfoxide: sucrose monooleate:pharmacologically active agent of from about 1:1:1 to 1:1:10 are preferred in such processes. Tetracycline hydrochloride and equilibrium mixtures of tetracycline hydrochloride and epi-tetracycline hydrochloride applied in this manner are especially efficacious in the treatment of acne.

Because of storage stability considerations relating to tetracycline hydrochloride and epi-tetracycline hydrochloride when formulated in solution, it is preferred herein to package anti-acne compositions prepared in the manner of this invention in kit form. That is to say, it is preferred herein to package the mixture of epi-tetracycline hydrochloride and tetracycline hydrochloride separately from the mixture of ethyl alcohol, water, sucrose monooleate and decyl methyl sulfoxide. Similar considerations also obtain when dealing with the other sugar esters, alcohols and penetration enhancing agents disclosed herein employed in combination with tetracycline hydrochloride and epi-tetracycline hydrochloride. Accordingly, a preferred embodiment of the present invention encompasses a separately packaged portion of an equilibrium mixture of tetracycline hydrochloride and epi-tetracycline hydrochloride as disclosed hereinabove, and a separately packaged portion of the penetration enhancing carrier of the present invention. Such separately packaged portions are stable on prolonged storage and can be admixed by the user immediately before the course of treatment. It is convenient to package sufficient quantities of the two portions to provide a sufficient quantity of the anti-acne composition to last for about 4 to about 8 weeks of treatment. This, of course, is not critical to the present invention inasmuch as the clinical efficacy of the compositions herein is satisfactory even after storage. However, the use of separate packages for the tetracycline hydrochoride plus epi-tetracycline hydrochloride equilibrium mixture and for the fluid ointment base insures that fresh material will be provided to the user.

The size of the kits herein is of no consequence to the practice of the invention. For example, such kits can be provided which contain only a few grams of material and which are suitable for but a single application. Alternatively, kits can be provided which comprise a relatively large volume of the penetration enhancing base and multiple packets of the mixture of tetracycline hydrochloride and epi-tetracycline hydrochloride. The user can then measure aliquots of the base and add thereto a premeasured packet of the antibiotic mixture. It is preferred herein to provide an anti-acne composition in kit form comprising a separately packaged, fluid ointment base comprising from about 0.1% to about 1% by weight of sucrose monooleate, from about 0.1% to about 8% by weight of decyl methyl sulfoxide, from about 30% to about 70% by weight of water, and from about 30% to about 70% by weight of ethyl alcohol. The second component of the kit comprises a separately packaged, dry portion of an anti-acne agent comprising an equilibrium mixture of tetracycline hydrochloride and epi-tetracycline hydrochloride in an amount sufficient to provide a 0.1% to 1.0% (wt.) concentration of said equilibrium mixture when dissolved in said fluid ointment base composition. Preferably, the equilibrium mixture of tetracycline hydrochloride and epi-tetracycline hydrochloride contains from about 0.05% to about 0.15% by weight (based on the total weight of all components) of a color stabilizer, especially sodium bisulfite. Alternatively, the second component can be an equivalent amount of either tetracycline hydrochloride or epi-tetracycline hydrochloride, since these materials are stable in the dry state. The following example illustrates such an anti-acne kit.

EXAMPLE XIV

| Component 1 | |
|---|---|
| Ingredient | Wt. |
| Tetracycline hydrochloride, epi-tetracycline hydrochloride equilibrium mixture | 0.06 oz. |
| Sodium bisulfite | 0.02 oz. |
| Component 2 | |
| Ethyl alcohol | 4 oz. |
| Sucrose monooleate | 0.06 oz. |
| Decyl methyl sulfoxide | 0.06 oz. |
| Water | 2.5 oz. |

In the composition of Example XIV, Component 1 is packaged in a dry, waterproof, foil packet; Component 2 is packaged in a bottle having sufficient headspace to allow mixing. Immediately prior to use, Component 1 is added to Component 2 and the mixture is shaken to mix. The user applies an effective amount of the composition to the acne lesion, ad lib, and alleviation of the acne is secured.

In the above composition, the mixture of tetracycline hydrochloride and epi-tetracycline hydrochloride is replaced by tetracycline hydrochloride and epi-tetracycline hydrochloride, respectively, and equivalent results are secured.

The preferred acne treatment of this invention comprises applying an effective amount of the composition of Examples IV or XIV to afflicted skin. Of course, it is preferred to cleanse the skin prior to treatment, and any soap or detergent composition suitable for washing the skin can be employed. However, it has surprisingly been discovered that, of the many detergents extant, sodium alkyl benzene sulfonate (avg. $C_{12}$ linear alkyl chain; commercial material) appears to enhance the anti-acne efficacy of the compositions herein. That is to say, acne lesions cleansed with an effective amount of an aqueous solution of sodium alkyl benzene sulfonate immediately prior to application of the anti-acne compositions herein are reduced in size and severity more rapidly than when the anti-acne composition is applied without pre-cleansing, or when such pre-cleansing is carried out with soaps or synthetic surfactants other than the sodium alkyl benzene sulfonate.

In a method aspect of this invention, acne lesions are treated by applying thereto an effective amount of an anti-acne composition comprising:
(1) from about 0.1% to about 1% by weight of sucrose monooleate;
(2) from about 0.1% to about 8% by weight of decyl methyl sulfoxide;
(3) from about 30% to about 70% by weight of water;
(4) from about 30% to about 70% by weight of ethyl alcohol; and
(5) from about 0.1% to about 1.0% by weight of a member selected from the group consisting of tetracycline hydrochloride, epi-tetracycline hydrochloride, and an equilibrium mixture of tetracycline hydrochloride and epi-tetracycline hydrochloride.

In a preferred method aspect, the acne lesions are first cleansed with an effective amount of an aqueous solution of sodium alkyl benzene sulfonate prior to application of an effective amount of the aforesaid anti-acne composition.

What is claimed is:
1. A composition in liquid or semi-liquid form adopted to topical application to animal tissue comprising:
(1) from about 0.05% to about 15% by weight of an astringent metal salt selected from the group consisting of
aluminum chlorhydrate,
zirconium oxychloride,
zinc chloride,
aluminum tribromide,
aluminum chloride ethanolate, and
a 1:1 mixture by weight of zirconium oxychloride and aluminum chlorhydrate;
(2) from about 0.1% to about 1.0 by weight of a sugar ester selected from the group consisting of
sucrose monooctanoate,
sucrose monodecanoate,
sucrose monolaurate,
sucrose myristate,
sucrose monopalmitate,
sucrose monostearate, sucrose monooleate, and
sucrose dioleate; and
(3) from about 0.1% to about 10.0% by weight of a sulfoxide compound selected from the group consisting of
octyl methyl sulfoxide,
nonyl methyl sulfoxide,
decyl methyl sulfoxide,
undecyl methyl sulfoxide,
dodecyl methyl sulfoxide,
2-hydroxydecyl methyl sulfoxide,
2-hydroxyundecyl methyl sulfoxide,
2-hydroxydodecyl methyl sulfoxide.

* * * * *